United States Patent [19]

Rose et al.

[11] Patent Number: 4,898,166
[45] Date of Patent: Feb. 6, 1990

[54] RESUSCITATION BAG CONTROL APPARATUS

[75] Inventors: Robert J. Rose, Easton, N.H.; Larry A. Sundsrud, Park Rapids, Minn.

[73] Assignee: Physician Engineered Products, Inc., Park Rapids, Minn.

[21] Appl. No.: 183,134

[22] Filed: Apr. 14, 1988

[51] Int. Cl.$^4$ .............................................. A62B 7/00
[52] U.S. Cl. ........................... 128/205.13; 128/205.14; 128/205.23
[58] Field of Search ...................... 128/205.13, 205.14, 128/205.16, 205.17, 205.23

[56] References Cited

U.S. PATENT DOCUMENTS

| | | | |
|---|---|---|---|
| 1,197,232 | 5/1916 | Pierpont | 128/205.13 |
| 1,202,125 | 10/1916 | Tullar | 128/205.13 |
| 2,217,575 | 10/1940 | Von Hoff | 128/205.14 |
| 2,300,273 | 10/1942 | Connell | 128/203 |
| 2,711,170 | 6/1955 | Bornstein | 128/203 |
| 2,850,010 | 9/1958 | Bennett et al. | 128/29 |
| 2,902,992 | 9/1959 | Renvall | 128/29 |
| 3,757,776 | 9/1973 | Bauman | 128/145.6 |
| 3,818,806 | 6/1974 | Fumagalli | 128/205.13 |
| 3,890,967 | 6/1975 | Elam et al. | 128/202 |
| 4,187,845 | 2/1980 | Dror | 128/205.13 |
| 4,297,999 | 11/1981 | Kitrell | 128/205.16 |

FOREIGN PATENT DOCUMENTS

| | | | |
|---|---|---|---|
| 18696 | of 1898 | United Kingdom | 128/205.14 |
| 1550720 | 8/1979 | United Kingdom | 128/205.14 |

Primary Examiner—Edgar S. Burr
Assistant Examiner—Aaron J. Lewis
Attorney, Agent, or Firm—Orrin M. Haugen; Thomas J. Nikolai; Frederick W. Niebuhr

[57] ABSTRACT

A controller for self-refilling resuscitation enclosures has a pair of arms pivotable between open and closed positions, an inside strap fixed to both arms, and an outside strap fixed to one arm. The outer strap can be releasably coupled at any one of a series of locations along the other arm, to selectively limit the amount of resuscitation bag recovery and thereby adjustably control the expansion or recovery volume of the enclosure. The straps, along with portions of the arm inside surfaces, maintain a contiguous wrapping engagement about the resuscitation enclosure throughout its compression and expansion, to positively secure the enclosure. The arms afford a mechanical advantage to reduce user fatigue, and provide for the tactile sensing of lung compliance during resuscitation.

14 Claims, 2 Drawing Sheets

RESUSCITATION BAG CONTROL APPARATUS

BACKGROUND OF THE INVENTION

This invention relates to artificial resuscitation devices, and more particularly to equipment for controlling the frequency and volume of air, oxygen or oxygen enriched air to a patient.

Cardiopulmonary resuscitation (CPR) is a standard technique applied to victims of cardiopulmonary arrest in order to re-establish normal cardiac and respiratory function. The respiration component of CPR is typically provided with an apparatus including a self-filling rubber or silastic enclosure or bag which is elastically compressible by hand, a face fitting mask in fluid communication with an outlet passage of the bag, and a one-way valve between the mask and bag to permit fluid passage only from the bag to the mask. The bag also has an inlet passage, typically with one opening for air and another, usually smaller opening for receiving oxygen. By hand-squeezing the bag, a clinician delivers air or oxygen to the patient, then releases the bag to permit it to expand to full size and thereby draw air or oxygen through the inlet passage.

Depending upon such factors as body size, age and sex, adult victims of cardiopulmonary arrest may require tidal volumes ranging from eight hundred to two thousand cubic centimeters, supplied to the lungs at a frequency of about twelve cycles or strokes per minute for adequate respiration. A further variable factor is the amount or concentration of oxygen required by a particular patient. The oxygen concentration and pH of a patient's blood must be adjusted to and maintained at a desired level for optimum response to drugs or other treatment administered during or after CPR. Accordingly, it is highly desirable to determine the tidal volume, respiration frequency and oxygen concentration during CPR.

Presently available portable artificial respiration equipment is not suitable for the desired monitoring and control of tidal volumes delivered by the hand-squeezed resuscitation bag. Although self-filling resuscitation enclosures can be selected on the basis of known volumes, the volume actually delivered can vary substantially among several operators, dependent upon such factors as hand size, technique, enthusiasm and fatigue. For example, in one test of twenty individuals, actual delivered volume, measured as an average of ten strokes or squeezes using the same capacity resuscitation bag, ranged from just over 700 cc's to nearly 1150 cc's when one hand was used, and ranged from just over 850 cc's to nearly 1400 cc's when two hands were employed. The same individual delivers varying volumes as well, primarily due to fatigue over an extended administration of CPR. Of course, the problem in measuring total supply of air or oxygen is aggravated if the frequency of squeezing the resuscitation bag is uncertain.

Equipment for controlling the amount of air and/or oxygen supplied during artificial resuscitation is known. For example, in U.S. Pat. No. 1,197,232 (Pierpont), air or oxygen from a portable tank is supplied to a patient through hand-operable bellows. A wing nut is adjustable on a curved rod spanning the bellows to adjust the extent to which they can be opened. U.S. Pat. No. 2,902,992 (Renvall) discloses a bellows between horizontal fixed and movable end plates. Volume control is provided in the form of a stop mounted on one of the rods supporting the movable plate.

U.S. Pat. No. 3,890,967 (Elam) discloses a dual bellows between a patient and a hand-squeezed resuscitation bag. One of the bellows has a cross-sectional area considerably smaller than the other, so that the arrangement can act as an amplifier for the squeeze bag. A scale is provided to indicate the amount of air supplied.

Similar apparatus can be employed to supply anesthesia gas, as disclosed in U.S. Pat. No. 3,757,776 (Bauman) and U.S. Pat. No. 4,187,845 (Dror). Dror shows a flexible cable linkage between a bellows and a foot pedal, while the Bauman Patent shows a pair of opposed concave paddles for squeezing a flexible breathing bag. The paddles are electrically operated to control the frequency of their opening and closing cycle. A related manner for frequency control is disclosed in U.S. Pat. No. 4,297,999 (Kitrell), in which a portable resuscitation apparatus includes a battery operated rhythm unit to indicate a prescribed beat, either visually or aurally.

While adequate for certain uses, the above devices fall short of optimum suitability for emergency cardiopulmonary arrest situations.

Therefore, it is an object of the present invention to provide a means to adjustably control the maximum volume assumed by a conventional self-filling resuscitation enclosure.

Another object is to provide a means for adjusting the delivered fluid volume of a self-refilling resuscitation bag, and its cycle frequency, in accordance with the needs of a particular patient.

A further object is to provide a device for retrofitting standard artificial resuscitation self-filling bags and associated equipment to more precisely control the tidal volume and level of oxygen.

Another object of the invention is to provide a device that ensures that a variety of individual clinicians will expel substantially the same volume of fluid during each compression/re-inflation cycle.

Yet another object is to provide a retrofit device for a standard artificial resuscitation bag which affords a mechanical advantage to reduce user fatigue, yet provides the clinician with a tactile sense of patient lung compliance during artificial respiration.

SUMMARY OF THE INVENTION

To achieve these and other objects, there is provided an apparatus for adjustably controlling the amount of fluid expelled from a self-recovering artificial resuscitation enclosure. The apparatus includes first and second arms, a connecting means mounted at a proximal end of each of the arms for pivotally connecting them, and a first strap of pliable, inextensible material fixed to a distal end portion of one of the arms. A coupling means removably couples an opposite end of the first strap to one of a plurality of discrete fastening locations along a distal end portion of the other arm. With the first strap and other arm coupled, the first and second arms and first strap are positioned in surrounding and contacting relation to a self-recovering resuscitation enclosure. The arms are pivotable between a closed position for elastically compressing the bag to a minimum fluid volume, and an open position corresponding to recovery of the resuscitation enclosure to one of a plurality of predetermined expansion volumes, each expansion volume corresponding to the coupling of the first strap at one of the fastening locations.

Preferably, a second strap of pliable and inextensible material is fixed at its opposite ends to the first and second arms, whereby the first and second straps cooperate to surround and contact the resuscitation enclosure. The straps on both sides of the bag are in surface contact with the bag and tend to maintain it in its desired mounting position in the apparatus.

The fastening means can include a plurality of substantially identical pairs of pegs integral with one of the arms, and a single pair of cap-like fasteners near the free end of the first strap, whereby each of the cap fasteners is positioned to selectively and nestingly engage an associated peg of a selected pair. Inflation volume indicia can be provided on the arm, proximate each pair of pegs, for indicating the resuscitation bag expansion volume associated with each pair.

Further, a cadence signaling device may be employed to assist the clinician in supplying air, oxygen or oxygen-enriched air at a frequency suited to the particular patient. In one form, the cadence indicator can comprise a power supply and a delay circuit, along with a lamp, buzzer or other signaling device electrically coupled to the power supply through the delay circuit.

To enhance ease of mounting and volume accuracy, the arms can be specially formed to match the contours of the resuscitation bag. This ensures a proper fit of the bag within the arms and straps, and further reduces the chance for slippage of the bag from its intended position.

To use the device, the clinician simply positions a conventional self-returning resuscitation bag between the arms and fixed strap, then fastens the adjusting strap at the location corresponding to the desired expansion volume. Then, the arms are closed upon one another by hand, and permitted to return to their open position under the influence of the residual elastic forces in the resuscitation bag. The arms can have a length selected to provide a mechanical advantage to reduce user fatigue, yet be sufficiently short to provide the clinician with a tactile sense of lung compliance during use. As a result the clinician is alerted immediately to any possible obstruction in air passages or the like, a substantial advantage as opposed to electrically powered resuscitation devices.

Moreover, the maximum expansion volume setting and timed compression cycles cooperate to ensure expulsion of a substantially uniform volume. The device is not subject to a variance in volume from features associated with direct hand-squeezing of the bag, for example hand size, hand strength, style of gripping (e.g. one or two hands), user enthusiasm and the like. The ease with which uniform volumes of air can be provided to a patient is of critical importance in hospital emergency room or emergency vehicle environments, where clinician attention must be directed as much as possible to the needs of the patient. Once the desired volume and cadence are set, there is no need to direct continued attention to the bag in an effort to approach, by judgment or guess, the desired tidal volume and cycle frequency.

IN THE DRAWINGS

For a better understanding of the above and other features and advantages, reference is made to the following detailed description and the drawings, in which.

DETAILED DESCRIPTION OF THE PREFERRED EMBODIMENTS

Figure 1:
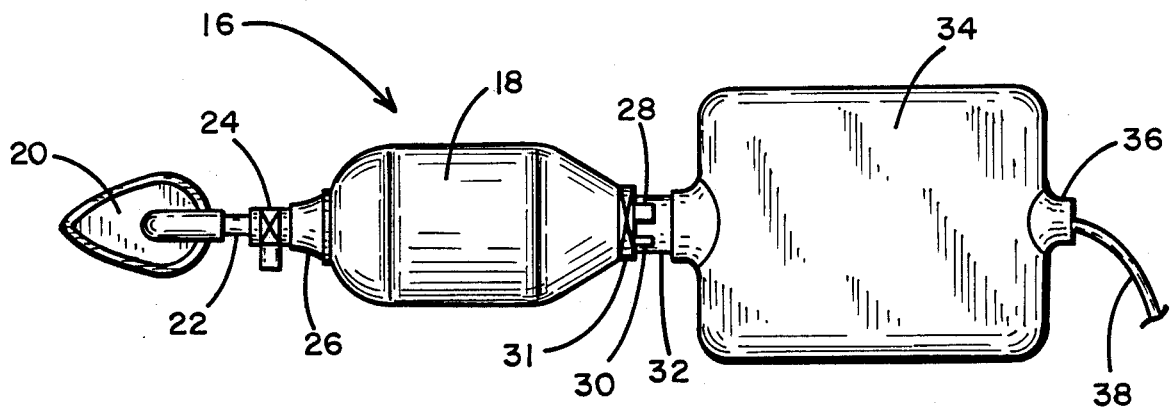
FIG. 1 is a plan view of a conventional artificial respiration device including a resuscitation enclosure.

Turning now to the drawings, there is shown in FIG. 1 an artificial respiration device 16 also known as a bag/valve/mask (BVM) device. The device includes a self-recovering enclosure or bag 18 constructed of rubber or silastic. Enclosure 18 is coupled to a face mask 20 through a length of tubing 22. The face mask is contoured for a reasonably comfortable fit over the mouth and nose of a patient during artificial respiration. Along the tubing is a one-way valve 24 for permitting passage of fluid from enclosure 18 to face mask 20, but preventing any backflow into the bag through an outlet passage 26 of the bag.

At the opposite end of the enclosure are two inlet passages, an air intake passage 28 and an oxygen intake passage 30 of smaller diameter, with a one-way valve means 31. As shown in FIG. 1, both inlet passages are surrounded by a sleeve 32 connecting enclosure 18 to an oxygen reservoir 34. An inlet neck 36 of the reservoir receives oxygen supplied over a supply tube 38 connected to a supply of oxygen, not illustrated.

Device 16 may be employed with oxygen reservoir 34 as shown, or without the reservoir, in which case tube 38 can be connected directly to oxygen intake passage 30. Alternatively, both passages 28 and 30 can be open to receive air. Thus, air, pure oxygen or oxygen-enriched air can be supplied to the patient as required.

Enclosure 18 is constructed of a size suitable for squeezing to supply air or oxygen to the patient. Due to the memory properties of the elastic material comprising the enclosure, it tends to re-assume the expanded or normal shape shown in FIG. 1 immediately after compression. When returning to its expanded configuration, enclosure 18 draws fluid exclusively through inlet passages 28 and 30 because of one-way valves 24 and 31. When fully expanded, enclosure 18 is ready for another stroke or hand-squeezing, and the compression/expansion cycle is repeated.

Beyond being sized for convenient hand compression, respiration enclosures are generally designed with a specific capacity in the range of from 1000 cc's to 1500 cc's for healthy adults, and with reduced size enclosures, for example 500 cc's, designed for children. Since the actual tidal volumes for healthy adults occupy a range of from 500 to 1000 cc's, resuscitation enclosures are offered with a corresponding range of capacities designed for hyperventilating a patient to supply oxygen rapidly under emergency conditions, in particular to counter metabolic acidosis by providing air and/or oxygen in sufficient quantity to restore the blood to a correct pH level.

Figure 2:
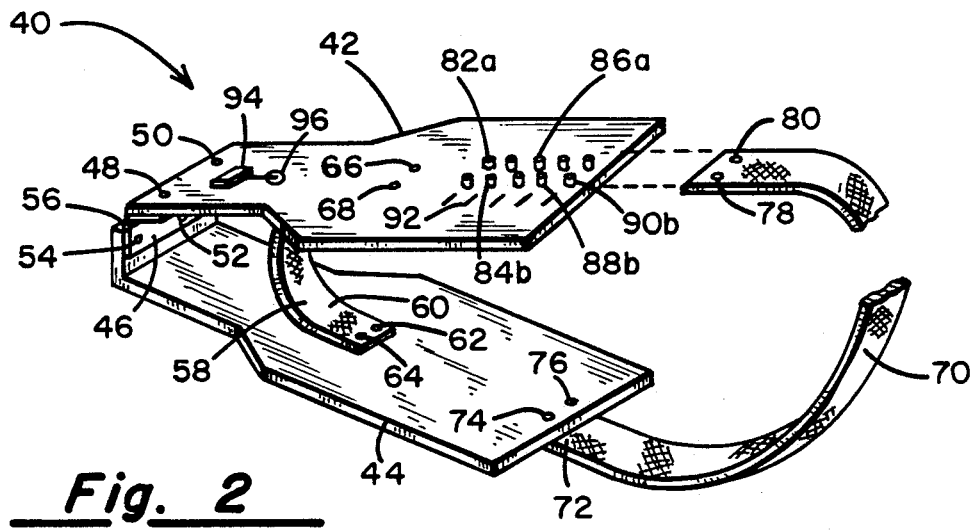
FIG. 2 is a perspective view of a controlling device for an artificial resuscitation enclosure constructed in accordance with the present invention.

Due to the variance in hand size and strength, fatigue and other factors noted above, selection of a properly sized resuscitation enclosure does not ensure that the desired tidal volume is delivered to the patient. To increase the consistency and accuracy of tidal volume delivered during each compression of the resuscitation enclosure, a resuscitation enclosure controller 40 is provided, as shown in FIG. 2. Controller 40 includes upper and lower rigid arms 42 and 44, respectively. The arms are connected pivotally with respect to one another by a hinge 46 fastened to the upper arm by fasteners 48 and 50, and to the lower arm by fasteners 52 and 54, which can be in the nature of rivets. Alternatively the hinge can be fastened to the arms with a suitable adhesive. A narrow central portion 56 of the hinge defines the pivot axis.

An inner strap 58 has a lower end portion 60 attached to lower arm 44 by fasteners 62 and 64, with an upper end of the inner strap being fastened to upper arm 42 by fasteners 66 and 68. An outer strap 70 is fastened at its lower end portion 72 to the lower arm by fasteners 74 and 76. Straps 58 and 70 are constructed to be pliable and inextensible, for example of a nylon reinforced plastic. Preferably the straps are textured as well, to enhance their ability to grip the surface of the resuscitation enclosure when surrounding it.

A pair of spaced apart cap-like snap fasteners 78 and 80 are provided at the outer end portion of outer strap 70. A series of complementary snap fasteners or rings are fixed to upper arm 42 and arranged in sets or pairs 82a/b-90 a/b, the fasteners in each set being spaced apart from one another and sized for a secure snap fit or engagement with fasteners 76 and 78. While snap fasteners are preferred as they are readily available, solid pegs could be utilized in lieu of rings, provided they are shaped for tight nesting with fasteners 78 and 80. Next to the rings is a scale 92. Illustrated simply as a series of five lines, scale 92 in practice can provide indicia, e.g. a series of tidal volume readings $O_2$ amount/concentration readings and the like, one corresponding to each set of rings 82 -90. In particular, an inner set of rings 82a and 82b corresponds to a minimum volume setting while the outer set of rings 90a and 90b corresponds to a maximum tidal volume.

A cadence indicator including a battery and delay microcircuit 94, and a light emitting diode 96, is mounted on the upper surface of upper arm 42 for convenient viewing during use. Through the delay circuit, LED 96 is periodically illuminated to indicate the desired frequency for respiration, for example twelve times per minute for adults and twenty times per minute for children. If desired, the circuit may be adjustable to provide intermediate cadences. A bell or other audible indication may be employed in lieu of or along with the LED.

Controller 40 is designed to at least generally correspond to the diameter of resuscitation bag 18. In particular, with outer strap 70 fastened with respect to the upper arm through one of the sets of rings, enclosure 18 is secured against sliding or other movement relative to the controller by virtue of a close wrapping engagement of straps 58 and 70 and inside surface portions of arms 42 and 44 about the enclosure. Further, controller 40 preferably corresponds in size to the diameter of enclosure 18 such that with strap 70 fastened to rings 90a and 90b and with the controller in an open position as shown in FIG. 3, enclosure 18 is permitted to expand to an expansion volume at or near full bag capacity.

Figure 4:
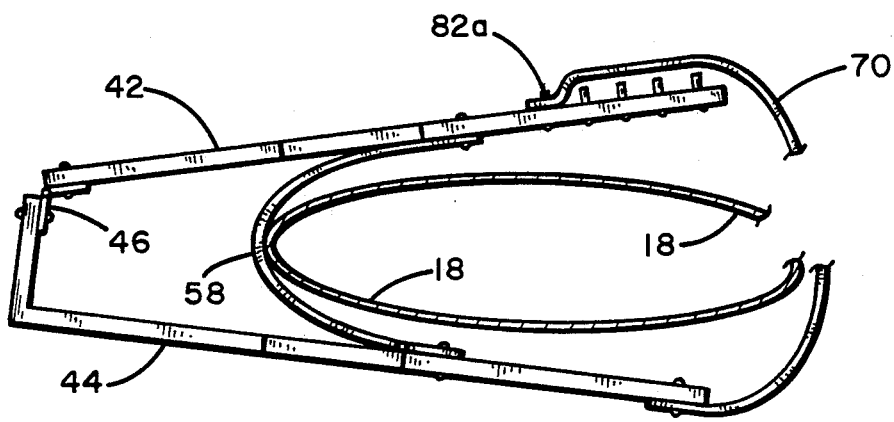
FIG. 4 is a view similar to that of FIG. 3, showing the device in a closed position corresponding to expelling fluid from the resuscitation enclosure.

To expel fluid from the resuscitation enclosure, arms 42 and 44 are simply pivoted toward one another to a closed position as illustrated in FIG. 4, thus to compress enclosure 18 to a minimum volume. It should be noted that regardless of whether the controller is in the open or closed position, the contiguous wrapping engagement of the straps and inner surface portions of the arms about enclosure 18 is maintained, due primarily to the pliable construction of straps 58 and 70. Hence, the resuscitation enclosure is securely maintained within the enclosure at all times during the compression/expansion cycle.

Figure 3:
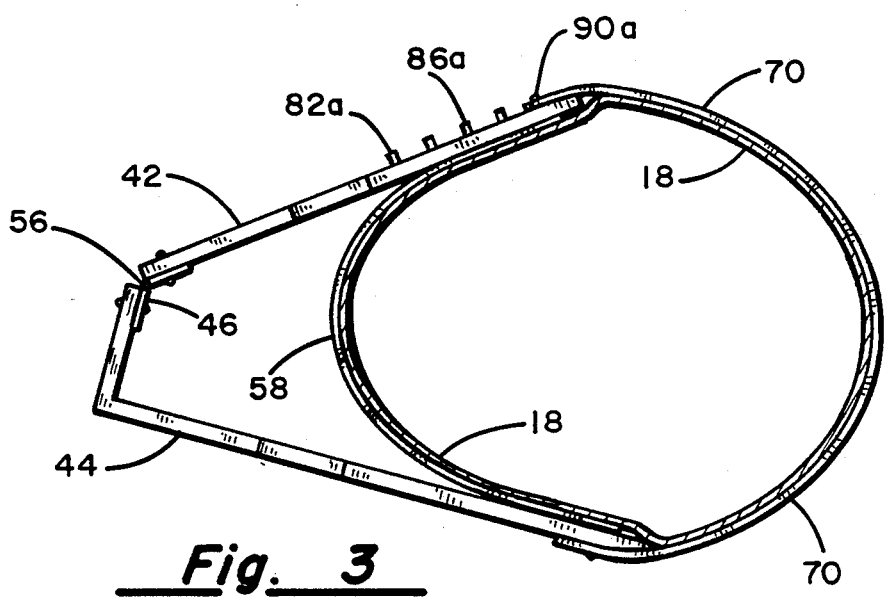
FIG. 3 is an elevation of the device of FIG. 2 in an open position showing the enclosure in section and at maximum enclosure expansion.
Figure 5:
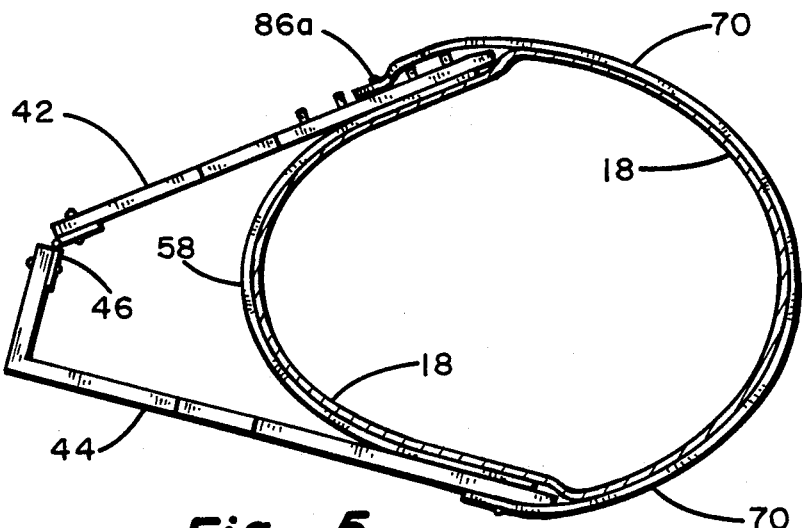
FIG. 5 is a view similar to that of FIG. 3, showing the device adjusted to an intermediate expansion level.

FIG. 5 illustrates controller 40 in its open position, but with outer strap 70 fastened to intermediate pair of rings 86a and 86b, whereby enclosure 18 is restrained to expand to an intermediate expansion volume less than that permitted by the setting illustrated in FIG. 3. For example, the full expansion volume in FIG. 3 can correspond to a tidal volume of 1400 cc's, with an intermediate expansion volume in FIG. 5 being 900 cc's. Typically the maximum setting would be appropriate for an adult male of large stature, with the intermediate setting appropriate for an adult of comparatively less stature and weight. Fastening strap 70 to innermost rings 82a and 82b would further restrict resuscitation bag 18 to an expansion of, for example, 400 cc's, an appropriate setting for children. Thus, controller 40 can be utilized to adjust the resuscitation enclosure to suit a wide variety of patients, eliminating the need for substitution of different sized resuscitation bags.

In using controller 40, the clinician or other provider would first rapidly assess the patient's body size, weight and any other attributes appropriate for properly estimating the appropriate tidal volume of air, oxygen or oxygen-enriched air. The clinician then mounts controller 40 in surrounding relation to resuscitation enclosure 18, selecting the appropriate pair of rings 82-90 in accordance with the desired expansion volume. Usually, oxygen will be provided at this point, through reservoir 34 or by connecting a supply of oxygen to intake passage 30. Finally, delay microcircuit 94 is actuated and adjusted to the desired cadence so that LED 96 will indicate the appropriate period between strokes. At this point the clinician, guided by signals from the cadence indicating light, periodically pivots arms 42 and 44 to the closed position to deliver the appropriate volume of air or oxygen to the patient.

During the resuscitation effort, the patient's blood can be monitored to determine the level of $O_2$, $CO_2$, its pH and any other appropriate parameters. As a result of such monitoring, it may be determined that the blood is either over-oxygenated or under-oxygenated, whereupon one or more of the following adjustments can occur:

the flow rate of oxygen into oxygen reservoir 34 or intake passage 30;
the cycle frequency; or
the tidal volume, by repositioning outer strap 70.

Thus, in addition to providing a controlled compression stroke to deliver a consistent tidal volume, controller 40 allows for adjusting the tidal volume for a controlled stroke at the new setting.

A further advantage of controller 40 resides in the fact that no extraneous power supply is required for compressing the resuscitation enclosure. Arms 42 and 44 are closed by hand, affording a mechanical advantage which can be increased by increasing their length. At the same time, the clinician is continuously touching the arms and therefore has tactile sense of lung compliance during artificial respiration. This enables the clinician to take immediate corrective action in the event of any discontinuity in respiration, caused for example by an air passageway restriction.

Figure 6:
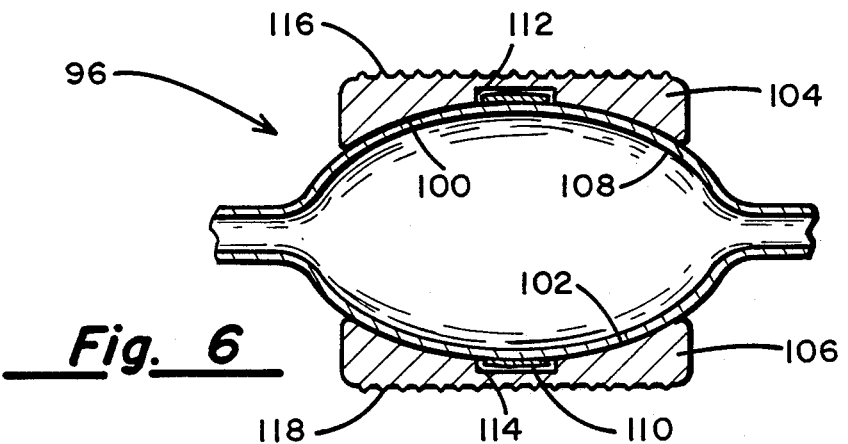
FIG. 6 is an end sectional view illustrating an alternative embodiment control device.

FIG. 6 illustrates an alternative embodiment controller 98 in end sectional view to show a number of features for providing a controller which is custom designed to suit a specific resuscitation enclosure. In particular, the inside surfaces 100 and 102 of arms 104 and 106, respectively are contoured to conform to the shape of a resuscitation enclosure or bag 108 when fully restored to its normal or fully inflated configuration. In addition, an inner strap 110 is fastened to arms 104 and 106 within respective recesses 112 and 114, to eliminate the possibility of fasteners presenting sharp points which might scratch or otherwise damage enclosure 108. Alternatively a suitable adhesive could secure the strap. Finally, outer surfaces 116 and 118 of the arms can be knurled or otherwise roughened for more positive hand-gripping of the controller to facilitate compression of bag 108. In other respects, controller 98 is substantially similar to controller 40.

Thus, in accordance with the present invention a standard resuscitation bag can be controlled to deliver a known tidal volume with a selected and controlled period between successive compression/reinflation cycles. A consistent tidal volume is maintained, regardless of differences among clinicians utilizing the device, and regardless of differences in handling by an individual clinician, for example due to fatigue. Given the variety of expansion volume settings, a single resuscitation bag can be employed to deliver a range of predetermined tidal volumes appropriate for adults and children. Also, the ability to control the tidal volume and delivery frequency enhances the ability to control the amount of oxygen delivered in the course of artificial respiration.

What is claimed is:

1. An apparatus for removably securing and adjustably controlling the volume of fluid expelled from a self-recovering artificial resuscitation enclosure, the apparatus including:
   first and second substantially rigid arms, and a connecting means mounted at a proximal end of each of said arms for pivotally connecting the arms for movement between closed and open positions;
   a first substantially inextensible and pliable strap member fixed at an end thereof to a distal end portion of said first arm and a second substantially inextensible and pliable strap member fixed at its opposite ends to said first and second arms, and cooperating with said strap member and said arms to form a surrounding, contiguous engagement with said resuscitation enclosure, said second strap being on the opposite side of the resuscitation enclosure from said first strap and between said enclosure and said connecting means;
   a fastening means for releasably coupling an opposite end of said first strap member at one of a plurality of discrete fastening locations along a distal end portion of said second arm, to releasably secure a self-recovering artificial resuscitation enclosure between said first and second arms, with said first and second arms and said first strap positioned in surrounding and contiguous relation to an outer surface of said resuscitation enclosure;
   said arms movable into said closed position to elastically compress said enclosure to a minimum fluid volume, and returning to said open position responsive to an elastic recovery of said resuscitation enclosure to one of a plurality of predetermined expansion volumes, each of said expansion volumes corresponding to the coupling of said first strap at one of said discrete fastening locations.

2. The apparatus of claim 1 wherein:
said fastening means includes a plurality of first snap fasteners integral with said second arm and arranged in discrete sets along said second arm, and at least one second snap fastener near the free end of said first strap member, each said second snap fastener adapted to selectively and nestingly engage an associated first snap fastener of a selected one of said discrete sets, each of said sets of first snap fasteners corresponding to one of said predetermined expansion volumes.

3. The apparatus of claim 2 further including:
indicia on said second arm and proximate said first snap fasteners, for indicating at least one predetermined expansion volume corresponding to each set of first snap fasteners.

4. The apparatus of claim 1 further including:
a cadence means for indicating a predetermined period between successive compression/reinflation cycles of said resuscitation enclosure.

5. The apparatus of claim 4 wherein:
said cadence means includes a light emitting diode, a source of electric power, and a delay circuit for electrically connecting said power source and said light emitting diode.

6. The apparatus of claim 1 wherein:
said first and second arms have generally concave first and second inside surfaces, respectively, said inside surfaces shaped to match the contours of said resuscitation enclosure.

7. The apparatus of claim 6, wherein
said end portions of said second strap member are mounted within first and second recesses formed respectively in said first and second arms.

8. The apparatus of claim 7 wherein:
the outer surfaces of said first and second arms are knurled to facilitate gripping of said arms by hand.

9. The apparatus of claim 3 further including:
a cadence means for indicating the predetermined period between successive compression/reinflation cycles of said resuscitation enclosure.

10. The apparatus of claim 2 wherein:
said first and second arms have generally concave first and second inside surfaces, respectively, said inside surfaces shaped to match the contours of said resuscitation enclosure.

11. A portable apparatus for removably securing and adjustably controlling the maximum volume of fluid expelled by compression of a self-recovering artificial resuscitation enclosure, said apparatus including:
   a first substantially rigid member, a second substantially rigid member, and a connecting means for joining said rigid members for movement with respect to one another between an open position and a closed position;
   a first inextensible and pliable strap means secured to said first and second rigid members and a second inextensible and pliable strap means secured at its opposite end portions thereof to said first and second rigid members, said first and second strap means cooperating with said rigid members to form a surrounding and contiguous engagement with an outer surface of a self-recovering artificial resuscitation enclosure with said second strap means being on the opposite side of said enclosure from said first strap means and between said self-recovering artificial resuscitation enclosure and said connecting means, thereby to releasably secure said resuscitation enclosure between said rigid members, with said rigid members movable into said closed position to cause an elastic compression of said resuscitation enclosure to a minimum fluid volume, said rigid members returning to said open position responsive to an elastic recovery of said resuscitation enclosure to one of a plurality of predetermined expansion volumes; and wherein said first strap means is releasably fastened to one of said rigid members at one of a plurality of discrete fastening locations on said one rigid member, each of said discrete fastening locations corresponding to one of said expansion volumes.

12. The apparatus of claim 11 wherein:
said first and second strap means include first and second inextensible and pliable straps connected to said rigid members and on opposite sides of said resuscitation enclosure when forming said contiguous engagement.

13. The apparatus of claim 12 wherein:
said first strap is fixedly coupled to said first rigid member and releasably coupled to the second rigid member, and said second strap is fixedly coupled to said first rigid member and to said second rigid member.

14. The apparatus of claim 13 wherein: said connecting means pivotably connects said first and second rigid members.

* * * * *